(12) United States Patent
Abdou et al.

(10) Patent No.: US 9,051,271 B2
(45) Date of Patent: Jun. 9, 2015

(54) SUBSTITUTED PYRIDINE DERIVATIVES USEFUL IN THE TREATMENT OF CANCER

(71) Applicant: United Arab Emirates University, Al-Ain (AE)

(72) Inventors: Ibrahim Mahmoud Abdou, Al-Ain (AE); Alaa ElDin Abdel Aziz Salem, Al-Ain (AE); Abdu Adem, Al-Ain (AE); Hussein F. Zhodi, Al-Ain (AE); Hany Abdel Aziz El Deab, Al-Ain (AE)

(73) Assignee: UNITED ARAB EMIRATES UNIVERSITY (AE)

( * ) Notice: Subject to any disclaimer, the term of this patent is extended or adjusted under 35 U.S.C. 154(b) by 3 days.

(21) Appl. No.: 14/074,973

(22) Filed: Nov. 8, 2013

(65) Prior Publication Data

US 2014/0128350 A1    May 8, 2014

(30) Foreign Application Priority Data

Nov. 8, 2012    (GB) .................................. 1220144.8

(51) Int. Cl.
  *A61K 31/655*    (2006.01)
  *C07D 213/85*    (2006.01)
  *A61K 45/06*    (2006.01)
(52) U.S. Cl.
  CPC ............ *C07D 213/85* (2013.01); *A61K 31/655* (2013.01); *A61K 45/06* (2013.01)
(58) Field of Classification Search
  CPC ........................... C07D 213/85; A61K 31/655
  USPC .......................................... 546/288; 514/344
  See application file for complete search history.

(56) References Cited

PUBLICATIONS

Dusan Mijin, Gordana Uscumlic, Nada Perisic-Janjic, Ivan Trkulja, Maja Radetic and Petar Jovancic, Synthesis, properties and colour assessment of some new 5-(3- and 4-substituted phenylazo)-4,6-dimethyl-3-cyano-2-pyridones, J. Serb. Chem. Soc. 71 (5) 435-444 (2006), accepted Mar. 3, 2005.

Valentic et al., "Linear Free Energy Relationships of the 13C NMR chemical shifts in 5-(3- and 4-substituted arylazo)-4,6-dimethyl-3-cyano-2-pyridones", ARKIVOC, 2009 (xiii), pp. 227-240, published Jan. 18, 2010.

Mijin et al., "Substituent and solvent effects on the UV/vis absorption spectra of 5-(3- and 4-substituted arylazo)-4,6-dimethyl-3-cyano-2-pyridones", Chemical Physics Letters, vol. 418, Issues 1-3, pp. 223-229, Jan. 2006.

Helal et al., "Synthesis and characterisation of a new series of pyridinone azo dyes for dyeing of synthetic fibers", Pigment & Resin Technology, vol. 33 issue 3, pp. 165-171, 2004.

Mijin et al. "The microwave-assisted synthesis of 5-arylazo-4,6-disubstituted-3-cyano-2-pyridone dyes", Dyes and Pigments vol. 85, Issues 1-2, Apr. 2010, pp. 73-78, (available online Oct. 29, 2009).

Alimmari et al., STN CAplus abstract for, "Synthesis, structure and solvatochromic properties of 3-cyano-4,6-diphenyl-5-(3- and 4-substituted phenylazo)-2-pyridones", STN CAplus accession No. 2010:1182956, Journal of the Serbian Chemical Society (2010), 75 (8) 1019-1032, May 10, 2010.

Alimmari et al., "Synthesis, structure and solvatochromic properties of 3-cyano-4,6-diphenyl-5-(3- and 4-substituted phenylazo)-2-pyridones", Journal of the Serbian Chemical Society (2010), 75 (8) 1019-1032, May 10, 2010.

Perisic-Janjic et al., RP TLC of some newly synthesized azo-dye derivatives, Journal of Planar Chromatography—Modern TLC, vol. 19, No. 108/Apr. 2006, pp. 98-103, first presented at the symposium "Planar Chromatography 2005" May 29-31, 2005.

*Primary Examiner* — Robert Havlin
(74) *Attorney, Agent, or Firm* — Katten Muchin Rosenman LLP

(57) ABSTRACT

The present invention describes compounds of formula (I)

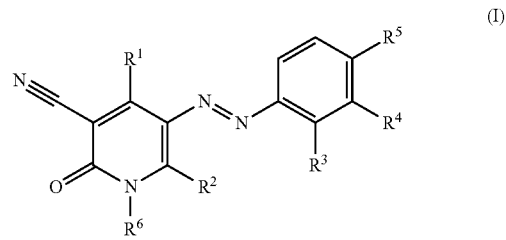

Wherein:
$R^1$ is selected from $C_1$-$C_6$ alkyl, $CF_3$, Phenyl & 2-thienyl
$R^2$ is selected from $C_1$-$C_6$ alkyl, phenyl & $CF_3$
$R^3$ is selected from H, $C_1$-$C_6$ alkyl, halo, $NO_2$, $NH_2$, haloalkyl
$R^4$ is selected from H, $C_1$-$C_6$ alkyl, halo, $NO_2$, $NH_2$, haloalkyl
$R^5$ is selected from H, $C_1$-$C_6$ alkyl, halo, $NO_2$, $NH_2$, haloalkyl
$R^6$ is selected from H, —$(CH_2)_nC(O)OR^7$ & $C(O)C_6H_4$—$R^7$
$R^7$ is selected from $C_1$-$C_6$ alkyl, phenyl optionally substituted by 1-3 substituents selected from $CF_3$, $NO_2$ and halo.
n is 0-6
These compounds have been identified as novel anticancer agents.

10 Claims, No Drawings

SUBSTITUTED PYRIDINE DERIVATIVES USEFUL IN THE TREATMENT OF CANCER

TECHNICAL FIELD

The invention relates to novel substituted pyridine derivatives useful in the treatment of cancer. This invention also relates to the use of such compounds in the treatment of cancer and to pharmaceutical compositions containing such compounds.

BACKGROUND ART

Compound 3-Cyano-4,6-dimethyl-5-(4'-nitrophenylazo)-pyridine-2(1H)-one was synthesised previously as per the following literature reference:

Dusan Mijin, Gordana Uscumlic, Nada Perisic-Janjic, Ivan Trkulja, Maja Radetic and Petar Jovancic, "Synthesis, properties and color assessment of some new 5-(3- and 4-substituted phenylazo)-,6-dimethyl-3-cyano-2-pyridones" J. Serb. Chem. Soc. 71 (5) 435-444 (2006)

SUMMARY OF THE INVENTION

The present invention relates to compounds of formula (I)

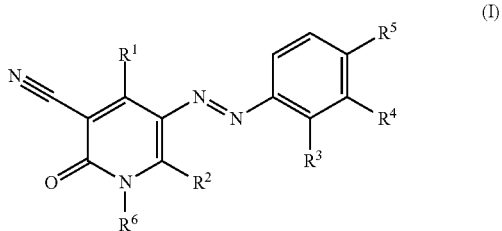

and to pharmaceutically acceptable salts and solvates thereof wherein:

$R^1$ is selected from $C_1$-$C_6$ alkyl, $CF_3$, Phenyl & 2-thienyl
$R^2$ is selected from $C_1$-$C_6$ alkyl, phenyl & $CF_3$
$R^3$ is selected from H, $C_1$-$C_6$ alkyl, halo, $NO_2$, $NH_2$, haloalkyl
$R^4$ is selected from H, $C_1$-$C_6$ alkyl, halo, $NO_2$, $NH_2$, haloalkyl
$R^5$ is selected from H, $C_1$-$C_6$ alkyl, halo, $NO_2$, $NH_2$, haloalkyl
$R^6$ is selected from H, —$(CH_2)_n$C(O)O$R^7$ & C(O)$C_6H_4$—$R^7$
$R^7$ is selected from $C_1$-$C_6$ alkyl, phenyl optionally substituted by 1-3 substituents selected from $CF_3$, $NO_2$ and halo.
n is 0-6
wherein, when $R^1$ & $R^2$ are both $CH_3$, $R^5$ is not $NO_2$, $CH_3$, $C_2H_5$, Cl, Br, I or H and $R^4$ is not $NO_2$, $CH_3$, $C_2H_5$, Cl, Br or H and when $R^1$ & $R^2$ are both phenyl, $R^5$ is not $NO_2$, Cl, Br, I or $CH_3$ and $R^4$ is not $NO_2$.

Where halo is defined as fluoro, chloro, bromo or iodo.
Where alkyl includes both straight chain and branched alkyl chains.

In a preferred embodiment, $R^1$ is $CH_3$, $CF_3$, Phenyl & 2-thienyl
In a particularly preferred embodiment, $R^1$ is $CH_3$
In a preferred embodiment $R^2$ is selected from $CH_3$, $CF_3$ and Phenyl
In a particularly preferred embodiment $R^2$ is selected from $CH_3$ and Phenyl
In a preferred embodiment $R^3$ is selected from H, halo, fluoroalkyl and $NO_2$
In a particularly preferred embodiment $R^3$ is selected from H, F and $NO_2$
In a most preferred embodiment $R^3$ is F
In another most preferred embodiment $R^3$ is H
In a preferred embodiment $R^4$ is selected from H, halo, fluoroalkyl and $NO_2$
In a particularly preferred embodiment $R^4$ is selected from H, F, $CF_3$ and $NO_2$
In the most preferred embodiment $R^4$ is H or $CF_3$
In a preferred embodiment $R^5$ is selected from H, halo, fluoroalkyl and $NO_2$
In a particularly preferred embodiment $R^5$ is selected from Cl, F, H, $CF_3$ and $NO_2$
In the most preferred embodiment $R^5$ is selected from F and $NO_2$
Preferably $R^6$ is H
Preferably $R^2$ is selected from $CH_3$, $CH_3CH_2$— and phenyl optionally substituted by 1-2 substituents selected from $CF_3$ and $NO_2$.
More preferably $R^7$ is selected from $CH_3$, $CH_3CH_2$—, phenyl, 3-$CF_3C_6H_4$, 4-$NO_2C_6H_4$ and 2,4-$(NO_2)_2C_6H_3$.
Preferably n is 0 or 1.
Particularly preferred compounds of the invention include:
3-Cyano-4,6-dimethyl-5-(2'-fluorophenylazo)-pyridine-2(1H)-one,
3-Cyano-4,6-dimethyl-5-(3'-trifluoromethylphenylazo)-pyridine-2(1H)-one,
3-Cyano-4,6-dimethyl-5-(4'-fluorophenylazo)-pyridine-2(1H)-one,
3-Cyano-4-methyl-6-phenyl-5-(2'-fluorophenylazo)-pyridine-2(1H)-one,
3-Cyano-4-methyl-6-phenyl-5-(3'-trifluoromethylphenylazo)-pyridine-2(1H)-one,
3-Cyano-4-methyl-6-phenyl-5-(4'-fluorophenylazo)-pyridine-2(1H)-one,
3-Cyano-4-methyl-6-phenyl-5-(4'-nitrophenylazo)-pyridine-2(1H)-one, Suitable salts include salts of acidic or basic groups present in compounds of formula (I). The compounds of formula (I) that are basic in nature are capable of forming a wide variety of salts with various inorganic and organic acids. The acids that may be used to prepare pharmaceutically acceptable acid addition salts of such basic compounds of formula I are those that form non-toxic acid addition salts. Suitable salts include acetate, benzenesulfonate, benzoate, bicarbonate, bisulfate, bitartrate, borate, bromide, calcium edentate, camsylate, carbonate, chloride, clavulanate, citrate, dihydrochloride edentate, edisylate, estolate, esylate, ethylsuccinate, fumarate, gluceptate, gluconate, glutamate, glycollylarsanilate, hexylresorcinate, hydrabamine, hydrobromide, hydrochloride, iodide isothionate, lactate, lactobionate, laurate, malate, maleate, mandelate, mesylate, methylsulfate, mucate, napsylate, nitrate, oleate, oxalate, pamoate, palmitate, pantothenate, phosphate, diphosphate, polygalacturonate, salicylate, stearate, subacetate, succinate, tannate, tartrate, teoclate, tosylate and valerate.

The subject invention also includes isotopically-labelled compounds which are identical to those described, but for the substitution of an atom for a corresponding isotope. Examples of isotopes include isotopes of hydrogen such as deuterium and tritium; isotopes of carbon such as $^{13}C$. Other examples are well known to those skilled in the art.

Where appropriate, compounds of the present invention include any cis/trans isomers.

The compounds of the present invention may be synthesized by a number of synthetic routes. Scheme 1 describes a conventional synthetic protocol for the synthesis of compounds of formula (I) where $R^6$ is H.

Scheme 1

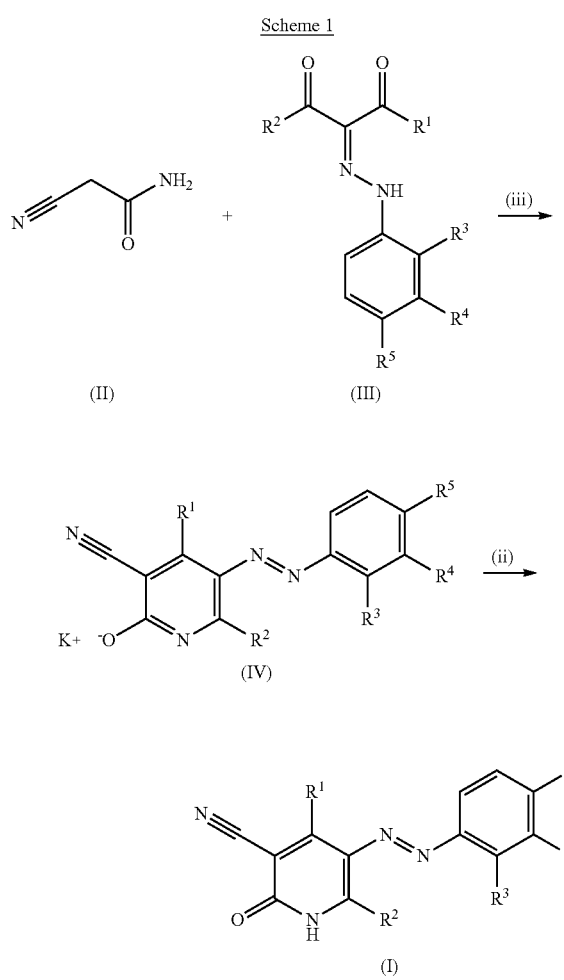

Compounds of formula (IV) may be synthesized by reacting compounds of formula (III) with cyanothioacetamide (II) under conditions of process step (i) treating the reaction mixture with potassium ethoxide in ethanol. Compounds of formula (I) may be obtained by treating the potassium salt (IV) with dilute acid, preferably 1.00 M HCl.

Compounds of formula (I) where $R^6$ is H, were also be made by the route described in Scheme 2 using microwave irradiation:

Scheme 2

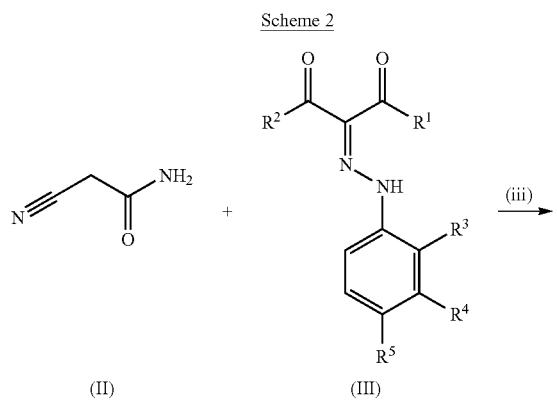

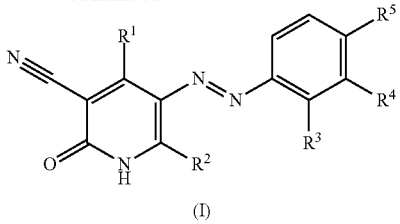

Compounds of formula (I) where $R^6$ is H, have been synthesized under reaction step (iii) by irradiating with microwaves a compound of Formula (III) in presences of cyanoacetamide (II) and potassium hydroxide.

Compounds of the general Formula (I) where $R^6$ is not H may be obtained by addition of the halide derivatives $X-(CH_2)_nC(O)OR^7$ or $X-C(O)C_6H_4-R^7$ to compounds (I) where $R^6$ is H.

This invention also relates to a method of treating cancer in a mammal comprising administering to said mammal an amount of a compound of formula (I):

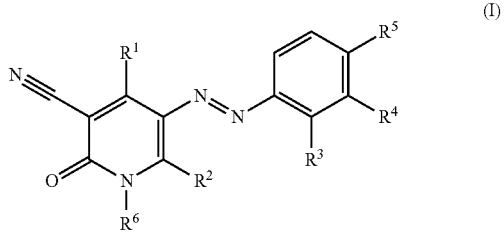

Wherein:
$R^1$ is selected from $C_1$-$C_6$ alkyl, $CF_3$, Phenyl & 2-thienyl
$R^2$ is selected from $C_1$-$C_6$ alkyl, phenyl & $CF_3$
$R^3$ is selected from H, $C_1$-$C_6$ alkyl, halo, $NO_2$, $NH_2$, haloalkyl
$R^4$ is selected from H, $C_1$-$C_6$ alkyl, halo, $NO_2$, $NH_2$, haloalkyl
$R^5$ is selected from H, $C_1$-$C_6$ alkyl, halo, $NO_2$, $NH_2$, haloalkyl
$R^6$ is selected from H, $-(CH_2)_nC(O)OR^7$ & $C(O)C_6H_4-R^7$
$R^7$ is selected from $C_1$-$C_6$ alkyl, phenyl optionally substituted by 1-3 substituents selected from $CF_3$, $NO_2$ and halo.
n is 0-6
or a pharmaceutically acceptable salt or solvate thereof.

In particular, the compounds are particularly useful in the treatment of breast cancer, lung cancer and colorectal cancer.

In preferred embodiments the mammal is a human.

In another preferred embodiment of the method the compounds of formula (I) are administered in combination with suitable anti-tumour or antineoplastic agents for the treatment of cancer, in particular for the treatment of breast, lung or colorectal cancers.

The term 'treatment' is intended to include curing, reversing, alleviating, palliative and prophylactic treatment of the condition Common cancers would include bladder, breast, colon, rectal, endometrial, kidney (renal cell), leukaemia, lung, melanoma, non-Hodgkin lymphoma, pancreatic, prostate, brain, skin, liver and thyroid cancers.

Patients suffering from cancer are commonly co-administered additional therapeutic agents, in particular suitable antineoplastic or anti-tumour agents. Suitable co-administrants would include:

1. Alkylating antineoplastic agents; such as Cisplatin, carboplatin, oxaliplatin, mechlorethamine, cyclophosphamide, chlorambucil & ifosfamide.

2. Plant alkaloids and terpenoids. These include:
   i. vinca alkaloids such as Vincristine, Vinblastine, Vinorelbine & Vindesine
   ii. Podophyllotoxin, etoposide and teniposide
   iii. Taxanes, such as paclitaxel, originally known as Taxol and Docetaxel
3. Topoisomerase inhibitors:
   i. type I topoisomerase inhibitors include camptothecins: irinotecan and topotecan
   ii. type II inhibitors include amsacrine, etoposide, etoposide phosphate, and teniposide
4. Cytotoxic antibiotics such as actinomycin, anthracyclines, doxorubicin, daunorubicin, valrubicin, idarubicin & epirubicin. Other cytotoxic antibiotics include bleomycin, plicamycin & mitomycin.

Other therapeutic agents are commonly administered to patients to deal with the side effects of chemotherapy. Such agents might include anti-emetics for nausea, or agents to treat anaemia & fatigue. Other such medicaments are well known to physicians and others skilled in cancer therapy.

The invention also relates to a pharmaceutical composition comprising a compound of formula (I) or pharmaceutically acceptable salt thereof and a pharmaceutically acceptable diluent or carrier.

Suitable composition forms include forms suitable for oral administration such as tablets, capsules, pills, powders, sustained release formulations, solutions, and suspensions; for parental injection such as sterile solutions, suspensions or emulsions; for topical administration such as ointments or creams; or for rectal administration such as suppositories.

Exemplary parenteral administration forms include suspensions or solutions in sterile aqueous solutions, for example aqueous propylene glycol or dextrose solutions. Such dosage forms can be suitably buffered, if desired.

Suitable pharmaceutical carriers include inert diluents or fillers, water and various organic solvents. Compositions may also include additional ingredients such as flavourings, binders & excipients. Tablets may include: disintegrates such as starch, alginic acid and complex silicates; binding agents such as sucrose, gelatin and acacia; and lubricating agents such as magnesium stearate, sodium lauryl sulfate and talc.

Solid compositions may also include soft and hard gelatin capsules. Preferred materials include lactose, milk sugar and high molecular weight polyethylene glycols.

Aqueous suspensions or elixirs may include sweetening or flavouring agents, colours and dyes, emulsifying agents, suspending agents as well as diluents such as water, ethanol, propylene glycol, glycerin or combinations thereof.

Methods of preparing various pharmaceutical compositions are well known to those skilled in the art. Reference is made to 'Remington's Pharmaceutical Sciences'.

EXPERIMENTAL

Equipment and Materials Used:
Microwave synthetic protocol was done using CEM Microwave system. Melting points were determined on (Pyrex capillary) Gallenkamp apparatus. Infrared spectra were recorded with a Thermo Nicolet Nexus 470 FT-IR spectrometer in the range 4000-400 $cm^{-1}$ on samples in potassium bromide disks. $^1$H-NMR spectra, $^{13}$C-NMR spectra and 2D-Ghmbc spectra were obtained on Varian Gemini 400 MHz FT NMR spectrometer in DMSO-$d_6$ at 60° C.; chemical shifts were recorded in $\delta$ (ppm) units, relative to tetramethylsilane (TMS) as an internal standard. The mass spectra were recorded on Shimadzu LCMS-QP 800 LCMS and AB-4000 Q-trap LC-MS/MS. Thin layer chromatography (TLC) was carried out on pre-coated Merck silica gel $F_{254}$ plates and UV light was used for visualization. Column chromatography was performed on Merck silica gel columns. All reagents were purchased from Aldrich and used without further purification. Elemental analyses were done at the Central Laboratories Unit, United Arab Emirates University.

Preparation

Scheme 3 shows the general scheme for the microwave and conventional synthetic protocols used for synthesizing claimed compounds Ia-Ih (Table 1). These compounds are characterised in that $R^6$ is H.

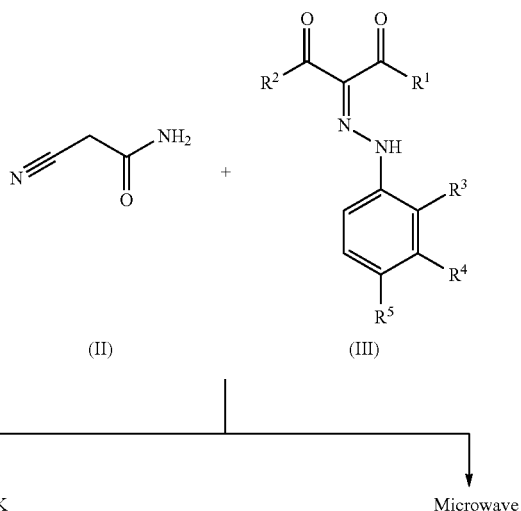

Scheme 3

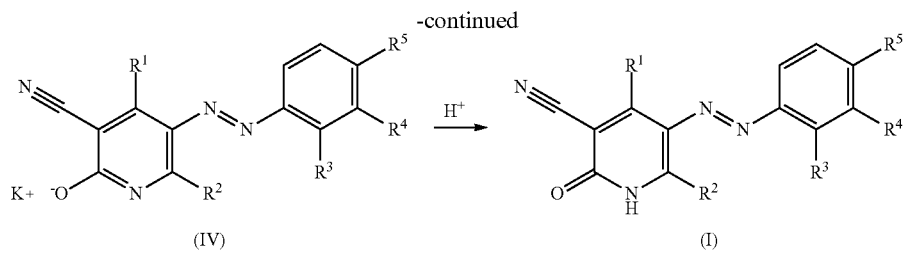

(IV) → (I)

Microwave Method

A mixture of equimolar amounts of cyanoacetamide (II) and the corresponding 2-arylhydrazono-1,3-disubstituted-propane-1,3-dione (III) (5.00 mmol) and potassium hydroxide (7.00 mmol) was irradiated at 200.00 W for an appropriate time (Table 1) in a 10.00 mL closed vial using CEM Microwave system. After completion of the reaction, as indicated by TLC, the obtained product was purified by crystallization from EtOH-DMF to afford the products ($I_{a-h}$).

Conventional Methods

A mixture of cyanothioacetamide (II) (0.01 mol) and the corresponding 2-arylhydrazono-1,3-disubstituted-propane-1,3-dione (III) (0.01 mol) was suspended in ethanol (30.00 mL) containing potassium ethoxide (0.68 g, 0.01 mol). The mixture was refluxed for 5.00 h, and then allowed to stand overnight. The resultant precipitate was filtered and crystallized from the appropriate solvent to give the corresponding solid product as potassium salt ($IV_{a-h}$). The resultant potassium salt was dissolved in water at 80° C., filtered and neutralized with dilute hydrochloric acid (1.00 M). The resulting solid product was collected by filtration and washed with distilled water to remove sodium chloride. The product was dried prior to crystallization from EtOH-DMF to afford the products ($I_{a-h}$).

Derivatives, reaction times and yields are listed in the table 1.

TABLE 1

| Compound No. | Compound (I) Substituents | | | | | | Microwave Synthesis Reaction | | Conventional Synthesis Reaction | |
| --- | --- | --- | --- | --- | --- | --- | --- | --- | --- | --- |
| | $R^1$ | $R^2$ | $R^3$ | $R^4$ | $R^5$ | $R^6$ | Time (min) | Yield (%) | Time (min) | Yield (%) |
| $I_a$ | $CH_3$ | $CH_3$ | F | H | H | H | 3.00 | 95 | 300.00 | 75 |
| $I_b$ | $CH_3$ | $CH_3$ | H | $CF_3$ | H | H | 3.00 | 93 | 300.00 | 79 |
| $I_c$ | $CH_3$ | $CH_3$ | H | H | F | H | 4.00 | 97 | 300.00 | 75 |
| $I_d$ | $CH_3$ | $C_6H_5$ | F | H | H | H | 4.00 | 97 | 300.00 | 75 |
| $I_e$ | $CH_3$ | $C_6H_5$ | H | $CF_3$ | H | H | 3.00 | 97 | 300.00 | 73 |
| $I_f$ | $CH_3$ | $C_6H_5$ | H | H | F | H | 4.00 | 94 | 300.00 | 77 |
| $I_g$ | $CH_3$ | $CH_3$ | H | H | $NO_2$ | H | 3.00 | 90 | 300.00 | 70 |
| $I_h$ | $CH_3$ | $C_6H_5$ | H | H | $NO_2$ | H | 4.00 | 91 | 300.00 | 74 |

Characterizing data for the synthesized compounds is provided below:

$I_a$; 3-Cyano-4,6-dimethyl-5-(2'-fluorophenylazo)-pyridine-2(1H)-one: mp 257° C.; IR (KBr, cm$^{-1}$) 3415 (NH), 2229 (CN), 1658 (CO); Ghmbc; $^1$H-NMR (400 MHz, DMSO-$d_6$) δ2.56 (s, 3H, $CH_3$), 2.58 (s, 3H, $CH_3$), 7.25-7.54 (m, 4H, Ar—H); $^{19}$F-NMR (400 MHz, DMSO-$d_6$): δ125.60-[−125.50] (m, 1F); $^{13}$C-NMR (400 MHz, DMSO-$d_6$) δ19.00 ($CH_3$), 20.10 ($CH_3$), 101.90 (C-5), 116.10 (C-1') 117.20 (C-3), 117.50 (C-3'), 117.70 (CN), 125.20 (C-5'), 132.10 (C-4'), 132.50 (C-6'), 132.60 (C-6), 153.30 (C-2'), 157.80 (C-2), 160.70 (C-4); LC-MS (ESI method): m/z 271 (M+H$^+$); Anal. Calcd for $C_{14}H_{11}FN_4O$: C, 62.22; H, 4.07; N, 20.74. Found: C, 62.05; H, 4.10; N, 20.95.

$I_b$; 3-Cyano-4,6-dimethyl-5-(3'-trifluoromethylphenylazo)-pyridine-2(1H)-one: mp 265° C.; IR (KBr, cm$^{-1}$) 3428 (NH), 2227 (CN), 1654 (CO); Ghmbc; $^1$H-NMR (400 MHz, DMSO-$d_6$) δ2.60 (s, 3H, $CH_3$), 2.62 (s, 3H, $CH_3$), 7.72-7.98 (m, 4H, Ar—H); $^{19}$F-NMR (400 MHz, DMSO-$d_6$): δ61.42 (S, $CF_3$); $^{13}$C-NMR (400 MHz, DMSO-$d_6$) δ18.40 ($CH_3$), 20.20 ($CH_3$), 102.50 (C-5), 115.70 (C-3), 119.00 (CN), 122.90 ($CF_3$), 125.70 (C-4'), 127.10 (C-2'), 130.60 (C-1'), 130.90 (C-5'), 131.10 (C-3'), 131.50 (C-6'), 131.50 (C-6), 155.60 (C-2), 159.80 (C-4); LC-MS (ESI method): m/z 319 (M−H$^+$); Anal. Calcd for $C_{15}H_{11}F_3N_4O$: C, 56.25; H, 3.44; N, 17.50. Found: C, 56.07; H, 3.53; N, 17.64.

$I_c$; 3-Cyano-4,6-dimethyl-5-(4'-fluorophenylazo)-pyridine-2(1H)-one: mp 272° C.; IR (KBr, cm$^{-1}$) 3436 (NH), 2225 (CN), 1653 (CO); Ghmbc; $^1$H-NMR (400 MHz, DMSO-$d_6$) δ2.57 (s, 3H, $CH_3$), 2.62 (s, 3H, $CH_3$), 7.32-7.37 (t, 2H, Ar—H, J=8.8 Hz), 7.79-7.83 (q, 2H, Ar—H, J=8.8 Hz); $^{19}$F-NMR (400 MHz, DMSO-$d_6$): δ110.16-[−110.10] (m, 1F); $^{13}$C-NMR (400 MHz, DMSO-$d_6$) δ18.70 ($CH_3$), 20.00 ($CH_3$), 101.90 (C-5), 116.10 (C-3), 116.60 (C-3'), 116.60 (C-5'), 116.80 (CN), 124.50 (C-2'), 124.60 (C-6'), 131.70 (C-6), 149.70 (C-1'), 160.50 (C-2), 162.60 (C-4'), 165.10 (C-4); LC-MS (ESI method): m/z 269 (M−H$^+$); Anal. Calcd for $C_{14}H_{11}F_3N_4O$: C, 62.22; H, 4.07; N, 20.74. Found: C, 62.47; H, 4.28; N, 20.49.

$I_d$; 3-Cyano-4-methyl-6-phenyl-5-(2'-fluorophenylazo)-pyridine-2(1H)-one: mp 225° C.; IR (KBr, cm$^{-1}$) 3427 (NH), 2225 (CN), 1656 (CO); Ghmbc; $^1$H-NMR (400 MHz, DMSO-$d_6$) δ2.63 (s, 3H, $CH_3$), 7.10-7.77 (m, 9H, Ar—H); $^{19}$F-NMR (400 MHz, DMSO-$d_6$): δ124.87-[−124.83] (m, 1F); $^{13}$C-NMR (400 MHz, DMSO-$d_6$) δ21.20 ($CH_3$),107.60 (C-5), 115.80 (C-1'), 116.20 (C-3), 117.20 (C-3'), 117.60 (CN), 125.10 (C-5'), 127.10 (C-4''), 128.10 (C-2''), 128.30 (C-6''), 128.80 (C-3''), 129.30 (C-5''), 130.70 (C-4'), 130.90 (C-6'), 133.30 (C-1''), 135.10 (C-6), 155.60 (C-2'), 158.50 (C-2), 160.10 (C-4); MS (ESI method): m/z 332 (M); Anal.

Calcd for $C_{19}H_{13}FN_4O$: C, 68.67; H, 3.92; N, 16.87. Found: C, 68.38; H, 4.01; N, 16.49.

$I_e$; 3-Cyano-4-methyl-6-phenyl-5-(3'-trifluoromethylphenylazo)-pyridine-2(1H)-one: mp 237° C.; IR (KBr, cm$^{-1}$) 3427 (NH), 2225 (CN), 1663 (CO); Ghmbc; $^1$H-NMR (400 MHz, DMSO-d$_6$) δ2.68 (s, 3H, CH$_3$), 7.43-7.74 (m, 9H, Ar—H); $^{19}$F-NMR (400 MHz, DMSO-d$_6$): δ61.62 (S, CF$_3$); $^{13}$C-NMR (400 MHz, DMSO-d$_6$) δ21.00 (CH$_3$), 104.40 (C-5), 115.80 (C-3), 117.80 (CN), 125.50 (CF$_3$), 127.00 (C-4'), 127.10 (C-2'), 127.90 (C-4''), 130.50 (C-2''), 130.50 (C-6''), 130.60 (C-3''), 130.60 (C-5''), 130.90 (C-1'), 130.90 (C-5'), 131.10 (C-3'), 131.10 (C-6'), 131.50 (C-1''), 132.30 (C-6), 154.50 (C-2), 160.20 (C-4); LC-MS (ESI method): m/z 382 (M); Anal. Calcd for $C_{20}H_{13}F_3N_4O$: C, 62.83; H, 3.40; N, 14.66. Found: C, 63.10; H, 3.26; N, 14.91.

$I_f$; 3-Cyano-4-methyl-6-phenyl-5-(4'-fluorophenylazo)-pyridine-2(1H)-one: mp 252° C.; IR (KBr, cm$^{-1}$) 3439 (NH), 2225 (CN), 1660 (CO); Ghmbc; $^1$H-NMR (400 MHz, DMSO-d$_6$) δ2.62 (s, 3H, CH$_3$), 7.23-7.51 (m, 9H, Ar—H); $^{19}$F-NMR (400 MHz, DMSO-d$_6$): δ109.604-[109.55] (m, 1F); $^{13}$C-NMR (400 MHz, DMSO-d$_6$) δ20.50 (CH$_3$), 102.10 (C-5), 115.80 (C-3), 116.50 (C-3'), 116.60 (C-5'), 116.80 (CN), 124.20 (C-4''), 124.50 (C-2''), 124.60 (C-6''), 127.90 (C-3''), 128.30 (C-5''), 129.30 (C-2'), 130.80 (C-6'), 132.10 (C-1''), 135.70 (C-6), 149.10 (C-1'), 160.00 (C-2), 162.70 (C-4'), 165.30 (C-4); LC-MS (ESI method): m/z 333 (M+H$^+$); Anal. Calcd for $C_{19}H_{13}FN_4O$: C, 68.67; H, 3.92; N, 16.87. Found: C, 68.41; H, 3.60; N, 17.05.

$I_g$; 3-Cyano-4,6-dimethyl-5-(4'-nitrothenylazo)-pyridine-2(1H)-one: mp>300° C.; IR (KBr, cm$^{-1}$) 3431 (NH), 2228 (CN), 1652 (CO); $^1$H-NMR (400 MHz, DMSO-d$_6$) δ2.67 (s, 3H, CH$_3$), 2.70 (s, 3H, CH$_3$), 7.94-7.96 (d, 2H, Ar—H, J=9.2 Hz), 8.36-8.39 (d, 2H, Ar—H, J=9.2 Hz).

Compound $I_g$ was synthesised previously as per the following literature reference:

Dusan Mijin, Gordana Uscumlic, Nada Perisic-Janjic, Ivan Trkulja, Maja Radetic and Petar Jovancic, "Synthesis, properties and color assessment of some new 5-(3- and 4-substituted phenylazo)-,6-dimethyl-3-cyano-2-pyridones" J. Serb. Chem. Soc. 71 (5) 435-444 (2006)

$I_h$; 3-Cyano-4-methyl-6-phenyl-5-(4'-nitronthenylazo)-pyridine-2(1H)-one: mp>300° C.; IR (KBr, cm$^{-1}$) 3436 (NH), 2225 (CN), 1663 (CO); $^1$H-NMR (400 MHz, DMSO-d$_6$) δ2.68 (s, 3H, CH$_3$), 7.45-7.46 (m, 5H, Ar—H), 7.53-7.56 (d, 2H, Ar—H, J=9.2 Hz), 8.21-8.23 (d, 2H, Ar—H, J=9.2 Hz).

Synthesis of 2-arylhydrazono-1,3-disubstitutedpropane-1,3-dione(s) (III)

To a solution of appropriate substituted acetone (0.01 mol) in 30.00 ml of ethanol, sodium acetate (3.00 g) was added. The mixture was cooled to 0° C. for 10.00 min. Cooled solution of arenediazonium chloride, prepared by the diazotization of 0.01 mol of the corresponding amine with the appropriate quantities of HCl and NaNO$_2$, was added with stirring. The reaction mixture was stirred for an additional one hour after which the solid precipitate was collected, washed with 2.00×10.00 ml of water and 2.00×10.00 ml of ethanol, and dried in the air.

Compounds' Activity:

Cell Culture and Viability Assay:

Human breast cancer cells MDA-MB-231 and colorectal cancer cells HT29, were maintained in DMEM medium (Invitrogen, Cergy Pontoise, France). Human lung cancer cells NCI-H460-Luc2 (Caliper Life Sciences, US) (NSCLC) were maintained in RPMI 1640 (Hyclone Thermo Scientific, MA United States). All media were supplemented with antibiotics (penicillin 50.00 U/ml; streptomycin 50.00 mg/ml) (Invitrogen, Cergy Pontoise, France) and 10.00% fetal bovine serum (FBS, Biowest, Nouaille, France).

Cells were seeded in 96-well plates at a density of 5,000 cells/well. After 24.00 hours of seeding, resultant cells' arrays were treated for 24.00-48.00 hours with increasing concentrations of the test compounds (5.00-100.00 μM), in triplicates. Control culture cells were treated with 0.10% DMSO.

The effect of the test compounds on cell viability was determined using a Cell Titer-Glo Luminescent Cell Viability assay (Promega Corporation, Madison, USA), based on quantification of ATP, which signals the presence of metabolically active cells. Luminescent signal was measured using GLOMAX Luminometer system. The data were presented as proportional viability (%) by comparing the treated group with the untreated cells, the viability of which is assumed to be 100%.

Effect of Tested Compounds on Cellular Viability:

The effects of investigated compounds at concentrations 5.00-100.00 μM on MDA-MB-231, NCI-H460-Luc2 and HT29 cells were investigated after 24.00 and 48.00 hours exposures. Cellular viability was found to decrease with increase in concentration and time. Inhibition rates ranged between 50.00 and 98.00% were recorded for all compounds at 100.00 μM concentration. The IC$_{50}$ is the concentration at which half-maximal inhibition occurs at 24 h. Approximate IC$_{50}$ value of 100.00 μM was obtained after 24.00 hours.

Inhibitions of the Cellular Viability by Different Compounds:

Exponentially growing MDA-MB-231, NCI-H460-Luc2 and HT29 cells were treated with vehicle (0.10% DMSO) and the indicated concentrations of investigated compounds. Viable cells were assayed as described in Materials and Methods. Exposure times of 24.00 and 48.00 hours were applied. All experiments were repeated at least three times.

Results

All the compounds of the invention have IC$_{50}$ activity of 72.50-482.80 μM against breast cancer cells.

All the compounds of the invention have IC$_{50}$ activity of 29.90-93.90 μM against colon cancer cells.

All the compounds of the invention have IC$_{50}$ activity of 29.80-35.93 μM against lung cancer cells.

Compounds $I_a$, $I_b$, $I_c$, $I_e$, $I_f$, $I_g$ and $I_h$ have IC$_{50}$ activities of 482.80, 270.50, 215.70, 90.49, 75.43, 72.36 and 171.70 μM against breast cancer cells.

Compounds $I_e$, $I_f$, $I_g$ and $I_h$ have IC$_{50}$ activities of 64.50, 93.91, 38.99 and 29.85 μM against colon cancer cells.

Compounds $I_e$, $I_f$, $I_g$ and $I_h$ have IC$_{50}$ activities of 35.93, 29.97, 29.77 and 30.72 μM against lung cancer cells.

The general efficacy of the compounds inducing cell death in different cancer cells is as follows: Lung cancer (NCI-H460-Luc2)>Colon cancer (HT29)>Breast cancer (MDA-MB-231)

The efficacy of the different compounds inducing cell death in colon cancer cells was as follows: $I_h$>$I_g$>$I_e$>$I_f$ The efficacy of the different compounds in inducing cell death in breast cancer was as follows: $I_g$=$I_f$>$I_e$>$I_n$>$I_c$>$I_b$>$I_a$ The efficacy of the different compounds in inducing cell death in lung cancer was as follows: $I_g$≈$I_f$≈$I_h$>$I_e$ Table of $IC_{50}$ values in μM
Micromole amounts of each compounds resulted in
the death of 50% of the cells; $IC_{50}$

| Compound | MDA-MB-231 Breast Cancer | HT29 Colon Cancer | NCI-H460-Luc2 Lung Cancer |
|---|---|---|---|
| $I_a$ | 482.80 | — | — |
| $I_b$ | 270.50 | — | — |
| $I_c$ | 215.70 | — | — |
| $I_d$ | — | — | — |
| $I_e$ | 90.49 | 64.50 | 35.93 |
| $I_f$ | 75.43 | 93.91 | 29.97 |
| $I_g$ | 72.36 | 38.99 | 29.77 |
| $I_h$ | 171.70 | 29.85 | 30.72 |

The invention claimed is:

1. A compound of formula (I)

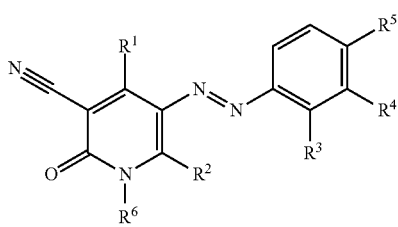

(I)

Wherein:
$R^1$ is selected from $C_1$-$C_6$ alkyl, $CF_3$, Phenyl & 2-thienyl
$R^2$ is selected from $C_1$-$C_6$ alkyl, phenyl & $CF_3$
$R^3$ is selected from H, $C_1$-$C_6$ alkyl, halo, $NO_2$, $NH_2$, haloalkyl
$R^4$ is selected from H, $C_1$-$C_6$ alkyl, halo, $NO_2$, $NH_2$, haloalkyl
$R^5$ is selected from, $C_1$-$C_6$ alkyl, F, $NO_2$, $NH_2$, haloalkyl
$R^6$ is selected from H, —$(CH_2)_n C(O)OR^7$ & $C(O)C_6H_4$—$R^7$
$R^7$ is selected from $C_1$-$C_6$ alkyl, phenyl optionally substituted by 1-3 substituents selected from $CF_3$, $NO_2$ and halo
n is 0-6
wherein, when $R^1$ & $R^2$ are both $CH_3$, $R^5$ is not $NO_2$, $CH_3$, $C_2H_5$, Cl, Br, I or H and $R^4$ is not $NO_2$, $CH_3$, $C_2H_5$, Cl, Br or H and when $R^1$ & $R^2$ are both phenyl, $R^5$ is not $NO_2$, Cl, Br, I or $CH_3$ and $R^4$ is not $NO_2$.

2. A compound of formula (I) as claimed in claim 1 wherein $R^1$ is $CH_3$.

3. A compound of formula (I) as claimed in any preceding claim wherein $R^3$ is selected from halo, fluoroalkyl and $NO_2$.

4. A compound of formula (I) as claimed in claim 1 wherein halo is F.

5. A compound of formula (I) as claimed in claim 1 wherein $R^2$ is selected from $CH_3$ and Phenyl.

6. A compound of formula (I) as claimed in claim 1 wherein $R^4$ is selected from halo, fluoroalkyl and $NO_2$.

7. A compound of formula (I) as claimed in claim 1 wherein $R^5$ is selected from F, fluoroalkyl and $NO_2$.

8. A method of treating cancer in a mammal comprising administering to said mammal an amount of a compound of formula (I)

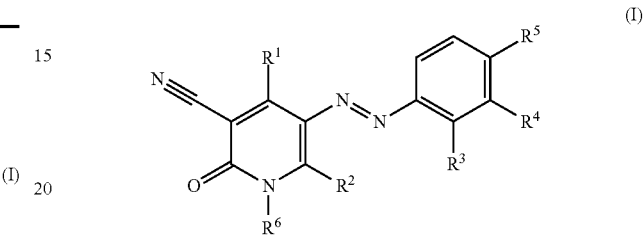

(I)

Wherein:
$R^1$ is selected from $C_1$-$C_6$ alkyl, $CF_3$, Phenyl & 2-thienyl
$R^2$ is selected from $C_1$-$C_6$ alkyl, phenyl & $CF_3$
$R^3$ is selected from H, $C_1$-$C_6$ alkyl, halo, $NO_2$, $NH_2$, haloalkyl
$R^4$ is selected from H, $C_1$-$C_6$ alkyl, halo, $NO_2$, $NH_2$, haloalkyl
$R^5$ is selected from, $C_1$-$C_6$ alkyl, F, $NO_2$, $NH_2$, haloalkyl
$R^6$ is selected from H, —$(CH_2)_n C(O)OR^7$ & $C(O)C_6H_4$—$R^7$
$R^7$ is selected from $C_1$-$C_6$ alkyl, phenyl optionally substituted by 1-3 substituents selected from $CF_3$, $NO_2$ and halo
n is 0-6
or a pharmaceutically acceptable salt or solvate thereof,
wherein the cancer is selected from bladder cancer, breast cancer, colon cancer, rectal cancer, endometrial cancer, kidney (renal cell) cancer, leukaemia, lung cancer, melanoma cancer, non-Hodgkin lymphoma cancer, pancreatic cancer, prostate cancer, brain cancer, skin cancer, liver cancer, and thyroid cancer.

9. The method as claimed in claim 8 wherein the compounds of formula (I) are administered in combination with suitable anti-tumour or antineoplastic agents.

10. A composition comprising (i) a compound of formula (I) as recited in any preceding claim and (ii) a pharmaceutically acceptable carrier or diluents.

* * * * *